United States Patent [19]

Chavkin et al.

[11] Patent Number: 4,975,269
[45] Date of Patent: Dec. 4, 1990

[54] SHELF STABLE ASPIRIN SOLUTIONS

[76] Inventors: Leonard Chavkin, R.R. 1, Box, 90, Bloomsbury, N.J. 08804; Leonard Mackles, 311 E. 23rd. St., New York, N.Y. 10010

[21] Appl. No.: 386,773

[22] Filed: Jul. 31, 1989

[51] Int. Cl.$^5$ .................... A61L 9/04; A61K 31/60; A61K 31/165
[52] U.S. Cl. .................... 424/45; 514/165; 514/617; 514/970
[58] Field of Search ............ 514/165, 159, 161, 617, 514/970; 424/45

[56] References Cited

U.S. PATENT DOCUMENTS

| | | | |
|---|---|---|---|
| 4,440,777 | 4/1984 | Zupan | 514/569 |
| 4,560,553 | 12/1985 | Zupan | 514/192 |
| 4,859,696 | 8/1989 | Kamiya et al. | 514/420 |

Primary Examiner—Douglas W. Robinson
Assistant Examiner—Raymond J. Henley, III
Attorney, Agent, or Firm—Omri M. Behr

[57] ABSTRACT

There is provided a shelf stable solution of aspirin, free of moieties reactive with aspirin, suitable for topical application to the skin compounded from aspirin, N,N-diethyl-m-toluamide USP (DEET), glyceryltriacetate USP (GTA), and acetic anhydride, provided that where GTA is present, at least 20 parts of DEET shall also be present and, after all components shall have been mixed, the resultant solution shall contain an initial amount of between about 1 and about 0.2 parts of acetic anhydride. The solution is made by preparing a solvent component consisting of at least N,N-diethyl-m-toluamide USP (DEET), and, if desired, glyceryltriacetate USP (GTA), provided that where GTA is present, at least 20 parts of DEET shall also be present, assaying said solvent mixture to determine the hydroxyl content, adding sufficient acetic anhydride to provide between about 1 and about 0.2 parts of unreacted acetic anhydride in the solution after dissolution of the aspirin therein, and dissolving aspirin, thereinto.

14 Claims, No Drawings

4,975,269

SHELF STABLE ASPIRIN SOLUTIONS

BACKGROUND OF THE INVENTION

The development of a topical form of aspirin has long been an objective of the formulator of pharmaceutical products and the fact that none exists today, is an indication of the difficulty of its fulfillment. In the minds of many experts, aspirin is still the drug of choice for the treatment of arthritis but the well known gastric irritation it produces, especially when taken in the large doses required for arthritis relief, remains the major bar to its more widespread use.

The major motivation for the development and success in the marketplace for acetaminophen and the host of non-steroidal anti-inflammatory drugs has been the hope of finding a mild analgesic without the gastric irritation produced by aspirin.

It is obvious that an effective topical form of aspirin would eliminate its gastric side effects. It is also accepted that the application locally of effective concentrations of aspirin could be effective in the treatment of musculoskeletal pain as in arthritis. Aspirin has been shown to be adsorbed into and through the skin and in fact the skin has been shown to be a reservoir for topically applied aspirin.

It is also known that aspirin is a more potent analgesic, anti-inflammatory agent than the other salicylates, e.g., methyl salicylate or triethanolamine salicylate which are the salicylates commonly used in topical analgesic products.

The major deterrent to the use of topical aspirin is that a stable aspirin solution has heretofore been impossible to prepare. Aspirin is not stable in aqueous solutions nor in any of the common solvents used in topical pharmaceuticals such as the glycols or lower aliphatic alcohols. It is rapidly hydrolyzed to acetic and salicylic acids and thus its shelf life in such solvents is far too short to permit the development of a stable aspirin solution suitable for marketing. Water alone is not the only contributor to aspirin degradation in solution. Aspirin will degrade by hydrolysis, glycolysis and trans-esterification, all of which will be promoted by any pH higher than about 3.5.

Solvents, such as N,N-Diethyl-m-Toluamide USP (DEET) and mixtures of N,N-Diethyl-m-Toluamide USP and Gyceryl Triacetate USP (GTA) give clear solutions of aspirin suitable for topical application to humans, in and of themselves, but both solvents cause aspirin to degrade to an unacceptable degree.

Both the DEET and glyceryl triacetate, if absolutely pure, would theoretically be unreactive to aspirin, but in reality, both these solvents as commercially available, contain impurities. The DEET is commercially available at about 97% active with the balance being isomers of DEET that have been identified as follows:
Methylbenzyl Alcohol
N,N,-Diethylbenzamide
N,-Ethyl Toluamide
N,N,-Diethyl-o-Toluamide
N,N,-Diethyl-p-Toluamide
Trimethyl biphenyl
Tetramethylbiphenyl These impurities are reactive to aspirin causing its degradation.

The glyceryl triacetate usually contains trace quantities of water and mono and diacetates of glycerine, all of which degrade aspirin.

SUMMARY OF THE INVENTION

There is provided a shelf stable solution of aspirin, free of moieties reactive with aspirin, suitable for topical application to the skin compounded from aspirin, 5–30 parts w/w, N,N-diethyl-m-toluamide USP (DEET), 20–95 parts w/w, glyceryl triacetate USP (GTA), 0–70 parts w/w, acetic anhydride, 0.2–2 parts w/w, to a total of 100 parts w/w, provided that where GTA is present, at least 20 parts of DEET shall also be present and, after all components shall have been mixed, the resultant solution shall contain an initial amount of between about 1 and about 0.2 parts of acetic anhydride.

The solution is made by preparing a solvent component consisting of N,N-diethyl-m-toluamide USP (DEET), 20–95 parts w/w, glyceryl triacetate USP (GTA), 0–70 parts w/w, provided that where GTA is present, at least 20 parts of DEET shall also be present, assaying said solvent mixture to determine the hydroxyl content, adding sufficient acetic anhydride to provide between about 1 and about 0.2 parts of unreacted acetic anhydride in the solution after dissolution of the aspirin therein, and dissolving aspirin, 5–30 parts w/w thereinto a total of 100 parts w/w. Such solutions have a shelf life of the order of 2 years.

The solutions disclosed herein may be compounded with other agents for the topical application of pharmaceutically active agents such as aerosol propellants and the like. Any of such agents known to the art may be employed provided that they do not contain moieties reactive with aspirin, in particular labile hydroxyl and carboalkoxy groups other than acetyl.

DESCRIPTION OF THE PREFERRED EMBODIMENTS

By reacting a small amount of acetic anhydride, ACS grade, with DEET or DEET/GTA and heating the system to from about 50° to about 80° C., specifically at about 70° C. for 30 minutes, the offending components of the solvents are neutralized. The aspirin is then dissolved in the treated solvents at about 40° C. Stable aspirin solutions are thus obtained. The amount of aspirin which can be dissolved in each solvent is a function of its solubility. If DEET is the sole solvent, up to 30% aspirin can be dissolved. If glyceryl triacetate is used as the co-solvent, lower amounts will dissolved, i.e., 15%.

The solutions mentioned above may be applied topically per se. They may also be compounded with unreactive propellants such as propane or nitrogen. The former would constitute 1–5% suitably about 3% w/w of the composition. In the latter case, the aerosol can is pressured to from about 80 to 120, suitably 100 psig (6–8.5, suitably 7 kg/cm$^2$) at ambient temperature, i.e. ca.20° C.

Since these compositions are topically safe, there is no upper dosage limit. They can be applied as needed to provide relief.

A series of experiments was conducted to determine the exact degree of aspirin stability with each solvent system. The percentages of aspirin and acetic anhydride used are varied. The determination of Free Salicylic Acid (FSA) as a percentage of the labeled amount of aspirin was the criterion for stability.

TEST/EXAMPLE 1

10% Aspirin in DEET, with varying amounts of acetic anhydride. The samples were stored at 40° C. for 3 months. The results are given as % FSA of label claim.

| % Acetic Anhydride | Initial | 1 mo @ 40° C. | 2 mo @ 40° C. | 3 mo @ 40° C. |
|---|---|---|---|---|
| 0.0 | 0.34 | 4.44 | 7.82 | 11.55 |
| 0.5 | 0.42 | 1.59 | 2.37 | 3.62 |
| 1.0 | 0.34 | 0.62 | 0.53 | 1.39 |

It can be seen that as the acetic anhydride concentration is increased, the % FSA decreases.

TEST/EXAMPLE 2

20% Aspirin in DEET, with varying amounts of acetic anhydride. The samples were stored at 40° C. for 3 months. The results are given as % FSA of label claim.

| % Acetic Anhydride | Initial | 1 mo @ 40° C. | 2 mo @ 40° C. | 3 mo @ 40° C. |
|---|---|---|---|---|
| 0.0 | 0.65 | 4.11 | 6.67 | 9.87 |
| 0.5 | 0.61 | 2.43 | 3.34 | 5.61 |
| 1.0 | 0.37 | 1.58 | 1.65 | 2.73 |

Again, it can be seen that as the acetic anhydride concentration is raised,, the % FSA decreases

TEST/EXAMPLE 3

10% Aspirin in 20% DEET and 70% glyceryl triacetate with varying amounts of acetic anhydride, stored at 40° C. for 3 months. The results are given as % FSA of label claim.

| % Acetic Anhydride | Initial | 1 mo @ 40° C. | 2 mo @ 40° C. | 3 mo @ 40° C. |
|---|---|---|---|---|
| 0.0 | 0.40 | 4.97 | 9.47 | 12.39 |
| 0.5 | 0.18 | 2.66 | 4.60 | 6.61 |
| 1.0 | 0.22 | 1.81 | 2.37 | 3.71 |

As the acetic anhydride concentration is increased, the % FSA decreases

TEST/EXAMPLE 4

15% Aspirin in 40% DEET and 45% glyceryl triacetate, with varying amounts of acetic anhydride, stored at 40° C. for 3 months. The results are given as % FSA of label claim.

| % Acetic Anhydride | Initial | 1 mo @ 40° C. | 2 mo @ 40° C. | 3 mo @ 40° C. |
|---|---|---|---|---|
| 0.0 | 0.60 | 5.00 | 8.87 | 12.11 |
| 0.5 | 0.39 | 2.27 | 3.78 | 6.53 |
| 1.0 | 0.32 | 1.96 | 2.28 | 3.95 |

As the acetic anhydride concentration is increased, the % FSA decreases.

From the foregoing, it can be seen that it is possible to stabilize the degradation of aspirin in the two solvents discussed by treating the solvents with between 0.1 and 2.0% with the preferred % between 0.5–1.0% of acetic anhydride so that stable solutions of between 1–30% with the preferred % between 10–20% of aspirin can be obtained.

EXAMPLE 5

Aerosol Composition

| Aspirin | 10 parts |
|---|---|
| Acetic Anhydride | 1 part |
| DEET | 86 parts |
| Propane | 3 parts |

A mixture of the DEET and the acetic anhydride is prepared and the aspirin dissolved therein. This solution is then charged to an aerosol can, equipped with an aerosol valve, to which the propane is added.

In accordance with the above procedure, but where in place of DEET per se, a mixture of 20 parts of DEET and 66 parts of GTA are used, a similar product is obtained.

EXAMPLE 6

Aerosol Composition

| Aspirin | 10 parts |
|---|---|
| Acetic Anhydride | 1 part |
| DEET | 89 parts |
| Nitrogen | to 100 psig/20° C. |

A mixture of the DEET and the acetic anhydride is prepared and the aspirin dissolved therein. This solution is then charged to an aerosol can, equipped with an aerosol valve, to which the nitrogen is added.

In accordance with the above procedure, but where in place of DEET per se, a mixture of 20 parts of DEET and 69 parts of GTA are used, a similar product is obtained.

We claim:

1. A shelf stable solution of aspirin, free of moieties reactive with aspirin, suitable for topical application to the skin compounded from:

| aspirin | 5–30 parts w/w |
|---|---|
| N,N-diethyl-m-toluamide USP | 20–95 parts w/w |
| glyceryl triacetate USP | 0–70 parts w/w |
| acetic anhydride | 0.2–2 parts w/w |
| to a total of | 100 parts w/w | provided that: when glyceryl triacetate is present, at least 20 parts of N,N-diethyl-m-toluamide is also present and, after mixing all components, the resultant solution immediately after compounding contains between about 0.2 to 1 part of acetic anhydride.

2. The solution of claim 1 wherein the solution is free of hydroxyl moieties and carboalkoxy moieties other than acetyl.

3. The solution of claim 1 additionally comprising an effective amount of an aerosol propellant free of moieties reactive with aspirin.

4. The solution of claim 3 wherein the excluded moieties reactive with aspirin are selected from the group consisting of hydroxyl moieties and carboalkoxy moieties other than acetyl.

5. The solution of claim 4 wherein the propellants comprise at least one member selected from the group consisting of nitrogen and propane 6. The shelf stable solution of aspirin of claim 1 which comprises:

| aspirin | 5-30 parts w/w and |
| N,N-diethyl-m-toluamide USP | 70-95 parts w/w. |

7. The shelf stable aerosol-dispensable solution of aspirin of claim 5 which comprises:

| aspirin | 5-30 parts w/w, |
| N,N-diethyl-m-toluamide USP | 70-95 parts w/w |
| propane | 1-5 parts w/w. |

8. The shelf stable aerosol-dispensable solution of aspirin of claim 5 which comprises:

| aspirin | 5-15 parts w/w, |
| N,N-diethyl-m-toluamide USP | 70-95 parts w/w |
| nitrogen | 80-120 psig/20° C. |

9. The shelf stable solution of aspirin of claim 1 which comprises:

| aspirin | 5-15 parts w/w, |
| N,N-diethyl-m-toluamide USP | 20-55 parts w/w and |
| glyceryl triacetate USP | 30-70 parts w/w. |

10. The shelf stable aerosol-dispensable solution of aspirin of claim 5 which comprises:

| aspirin | 5-15 parts w/w, |
| N,N-diethyl-m-toluamide USP | 20-55 parts w/w and |
| glyceryl triacetate USP | 30-70 parts w/w |
| propane | 1-5 parts w/w. |

11. The shelf stable aerosol-dispensable solution of aspirin of claim 5 which comprises:

| aspirin | 5-15 parts w/w, |
| N,N-diethyl-m-toluamide USP | 20-55 parts w/w and |
| glyceryl triacetate USP | 30-70 parts w/w |
| nitrogen | 80-120 psig/20° C. |

12. A method of making a shelf stable solution of aspirin, free of moieties reactive with aspirin, in a medium suitable for topical application to the skin which comprises:
(a) preparing a solvent component consisting of:

| N,N-diethyl-m-toluamide USP | 20-95 parts w/w |
| glyceryl triacetate USP | 0-70 parts w/w | provided that when glyceryl triacetate is present, at least 20 parts of N,N-diethyl-m-toluamide is also present,
(b) assaying said solvent mixture to determine the hydroxyl content,
(c) adding sufficient acetic anhydride to provide between about 0.2 to 1 part of unreacted acetic anhydride in the solution after the subsequent step of dissolution of the aspirin therein and
(d) dissolving 5-30 parts w/w of aspirin therein to a total of 100 parts w/w.

13. The method of claim 12 wherein the solvent component consists of:

| N,N-diethyl-m-toluamide USP | 20-55 parts w/w, |
| glyceryl triacetate USP | 30-70 parts w/w, |
| and the amount of aspirin is | 5-15 parts w/w, |
| to a total of | 100 parts w/w. |

14. The method of claim 12 wherein the solvent component consists of:

| N,N-diethyl-m-toluamide USP | 70-95 parts w/w, |
| and the amount of aspirin is | 5-30 parts w/w, |
| to a total of | 100 parts w/w. |

* * * * *